United States Patent [19]

Nefedov et al.

[11] 4,207,212
[45] Jun. 10, 1980

[54] CATALYST FOR CARBONYLATION OF AROMATIC NITROCOMPOUNDS

[76] Inventors: Boris K. Nefedov, ulitsa Shosseinaya, 9, kv. 64, Moscow; Jury I. Dergunov, prospekt Pobedy, 3, kv. 39; Anatoly I. Rysikhin, prospekt Pobedy, 3, kv. 7, both of Dzerzhinsk Gorkovskoi oblasti; Vladimir I. Manov-Juvensky, ulitsa Angarskaya, 1, korpus 3, kv. 72, Moscow; Georgy P. Balabanov, ulitsa Tereshkovoi, 64-a, kv. 58, Dzerzhinsk Gorkovskoi oblasti; Khakberdy O. Khoshdurdyev, ulitsa Ostrovityanova, 33-a, kv. 159, Moscow, all of U.S.S.R.

[21] Appl. No.: 19,750

[22] Filed: Mar. 12, 1979

[51] Int. Cl.² .................. B01J 23/28; B01J 23/44; B01J 23/58; B01J 23/64

[52] U.S. Cl. .................. 252/468; 260/453 PC
[58] Field of Search .................. 252/468; 260/453 PC

[56] References Cited

U.S. PATENT DOCUMENTS

| 3,523,964 | 8/1970 | Kober et al. .................. 252/470 X |
| 3,637,786 | 1/1972 | Smith .................. 260/453 PC |
| 3,823,174 | 7/1974 | Hammond et al. .................. 260/453 PC |
| 3,828,089 | 8/1974 | Hammond et al. .................. 260/453 PC |

Primary Examiner—W. J. Shine
Attorney, Agent, or Firm—Lackenbach, Lilling & Siegel

[57] ABSTRACT

The catalyst for carbonylation of aromatic nitrocompounds according to the present invention contains 1.6 to 4.0% by weight of magnesium oxide, or calcium oxide, or zinc oxide; 48.8 to 77.0% by weight of palladium oxide; molybdenum oxide being the balance.

3 Claims, No Drawings

CATALYST FOR CARBONYLATION OF AROMATIC NITROCOMPOUNDS

FIELD OF THE INVENTION

The present invention relates to processes for carbonylation of aromatic nitrocompounds and, more specifically, to catalysts for carbonylation of aromatic nitrocompounds to mono- and diisocyanates.

The process according to the present invention is useful in the production of, for example, mono- and diisocyanates which are widely employed in the manufacture of polyurethane articles and pesticides.

Known in the art is a catalyst employed for carbonylation of 2,4-dinitrotoluene comprising a mixture of a palladium complex with isoquinoline $Pd[C_9H_9N]_2Cl_2$ taken in an amount ranging from 50 to 75% by weight in dichlorobenzene and a compound including iron and molybdenum $Fe_2Mo_7O_{24}$ taken in an amount within the range of from 25 to 50% by weight. There is obtained 2,4-toluylenediisocyanate in a maximum yield of 70% at a 100% conversion of the starting compound, i.e. 2,4-dinitrotoluene (cf. FRG Pat. No. 2,165,355).

Furthermore, it is known that upon carbonylation of 2,4-dinitrotoluene in the presence of a homogeneous-heterogeneous catalyst consisting of 20–30% by weight of palladium chloride and 50–60% by weight of pyridine with the addition of 10–40% by weight of oxides of iron, molybdenum or $Fe_2Mo_7O_{24}$ there is obtained 2,4-toluenediisocyanate in a yield of 21–76% at a 83–100% conversion of the starting compound (cf. French Pat. No. 2,120,110).

Also known in the art are catalysts for carbonylation of aromatic compounds containing 50–60% by weight of Pd (pyridine)$_2$ Cl$_2$ and 40–50% by weight of MoO$_3$ (U.S. Pat. No. 3,823,174); 25–75% by weight of Pd (pyridine)$_2$Cl$_2$ and 25–75% by weight of MoO$_3$ or Pd(pyridine)$_2$Cl$_2$ and 25–75% by weight of Cr$_2$O$_3$/Al$_2$O$_3$ (U.S. Pat. No. 3,828,089) in the presence of which catalysts 2,4-toluenediisocyanate is produced from 2,4-dinitrotoluene in a yield of 10 to 68% at a conversion of the starting material of 50 to 68%.

The best homogeneous-heterogeneous catalyst for the synthesis of aromatic monoisocyanates, in particular phenylisocyanate, is PdCl$_2$(60–75%)–V$_2$O$_5$(25–40%) in the presence of which catalyst phenylisocyanate is produced in a yield of 82–90% at a conversion of nitrobenzene of 90–100% (cf. U.S. Pat. No. 3,523,964).

Said prior art catalysts have certain disadvantages such as indefiniteness of the catalyst composition, the presence of palladium chloride in the liquid phase which necessitates a complicated system for its separation and regeneration, an insufficient selectivity and, consequently, an insufficient yield of the desired product.

Also known in the art is a heterogeneous catalyst used in the synthesis of isocyanates which contains halides of palladium, rhodium, iridium, platinum, rhenium, ruthenium or mixtures thereof deposited onto alumina, silica gel, activated carbon or barium sulphate and oxides of vanadium, molybdenum, tungsten, niobium, chromium, titanium, tantalum (cf. U.S. Pat. No. 3,637,786).

This prior art catalyst has a disadvantage residing in its low activity (conversion of the nitrocompound is 53 to 77%) and selectivity (the desired product yield is not more than 21%).

It is the main object of the present invention to provide a catalyst for carbonylation of aromatic nitrocompounds which would have increased activity and would ensure increased selectivity.

SUMMARY OF THE INVENTION

This object is accomplished by a catalyst for carbonylation of aromatic nitrocompounds to mono- and diisocyanates consisting of 1.6 to 4.0% by weight of an oxide of a metal selected from the group consisting of magnesium, calcium, zinc; 48.8–77.0% by weight of palladium oxide, 49.6–19% by weight of molybdenum oxide.

The present invention now enables carbonylation of aromatic nitrocompounds to mono- and di-isocyanates at high conversion of the starting compound equal to 100% and an increased yield of the desired product as high as 98–99%.

DETAILED DESCRIPTION OF THE INVENTION

The catalyst according to the present invention is intended for carbonylation of aromatic nitrocompounds to mono- and di-isocyanates, such as 2,4-toluenediisocyanate, phenylisocyanate, and derivatives thereof.

The catalyst according to the present invention consists of 1.6 to 4.0% by weight of magnesium oxide, or calcium oxide, or zinc oxide; 48.8 to 77% by weight of palladium oxide and 49.6 to 19% by weight of molybdenum oxide.

It has been experimentally found that the amounts of the catalyst components taken beyond the above-specified limits result in a sharply reduced yield of the desired product. The above-specified weight amounts of the catalyst components define the range of optimal activity and selectivity of the catalyst.

In accordance with the present invention the catalyst can be supported on a carrier such as alumina, silica, aluminosilicate which results in an increased mechanical strength of the catalyst and contributes to savings on expensive materials used as the catalyst ingredients.

It is advisable that the carrier employed in accordance with the present invention be present in an amount ranging from 76.7 to 85.1% by weight of the catalyst.

As it has been already mentioned hereinabove, the catalyst according to the present invention is intended for carbonylation of aromatic nitrocompounds and requires no variation of the previously established process conditions, since carbonylation is performed at a temperature within the range of from 165° to 210° C. under the pressure of 300 atm. The time of carbonylation is equal to 2 hours.

It has been found experimentally that the activity and selectivity of the catalyst of the present invention are substantially higher than those of the prior art catalysts. These improvements are attributed to an increased stability of isocyanate in the presence of oxides of magnesium, calcium or zinc; this, in turn, results in lowered resinification which, as it has been found, is responsible for lowered values of activity and selectivity.

EXAMPLE 1

0.2 g of palladium oxide powder (particle size of 60–80 mesh) is mixed with 0.2 g of powder-like molybdenum oxide (particle size of 60–80 mesh) and with 0.005 g of powder-like magnesia (particle size 60–80 mesh), said powders of the above-mentioned oxides have been preliminary dehydrated by heating in a current of air over 5 hours at a temperature of 500° C. The resulting mixture is thoroughly blended and then compression-molded into tablets. Thereafter, the tablets are ground to give grains of an irregular shape with dimensions of about 1×1 mm containing 49.2% by weight of palladium oxide, 49.2% by weight of molybdenum oxide and 1.6% by weight of magnesium oxide.

Into a 0.15 l autoclave there are charged 10 ml of o-dichlorobenzene, 2 g of 2,4-dinitrotoluene, 0.2 ml of pyridine and 0.2 g of the catalyst produced above in the form of grains. The autoclave is purged with carbon monoxide, whereafter the pressure of carbon monoxide is increased to 300 atm and heating is effected for 2 hours at a temperature of 190° C.

The liquid reaction products, after separation of the catalyst, are subjected to analysis by the method of gas-liquid chromatography. 1.8 g of 2,4-toluylenediisocyanate are recovered by rectification which corresponds to a 90% yield of the desired product (boiling point is 121° C./10 mm Hg; $n_D^{20} = 1.567$). Conversion of the starting compound, i.e. 2,4-dinitrotoluene, is 100%.

EXAMPLE 2

Powders of 0.2 g of palladium oxide, 0.2 g of molybdenum oxide, 0.01 g of calcium oxide preliminarily dehydrated by calcination in a current of air over a period of 5 hours at a temperature of 500° C. are thoroughly intermixed and compression molded into tablets. The thus-produced tablets are crushed to give grains with an approximate size of 1×1 mm and containing 48.8% by weight of palladium oxide, 48.8% by weight of molybdenum oxide and 2.4% by weight of calcium oxide.

Carbonylation of 2,4-dinitrotoluene is effected under conditions similar to those described in the foregoing Example 1, using the catalyst with the composition specified in this Example. 1.83 g of 2,4-toluylenediisocyanate are recovered by rectification (the yield is 92%); the starting 2,4-dinitrotoluene has reacted by 100%.

EXAMPLE 3

Powders of palladium oxide (0.27 g), molybdenum oxide (0.0665 g) and zinc oxide (0.014 g) preliminarily dehydrated by calcination in a current of air at a temperature of 500° C. for the period of 5 hours are intermixed and compression-molded into tablets. The resulting tablets are crushed to grains with an approximate size of 1×1 mm containing 77.0% by weight of palladium oxide, 19% by weight of molybdenum oxide and 4.0% by weight of zinc oxide.

Carbonylation of 2,4-dinitrotoluene is performed under conditions similar to those described in the foregoing Example 1 using the catalyst as prepared in the present Example.

1.98 g of 2,4-toluylenediisocyanate are recovered by rectification (the yield is equal to 99%); the conversion of the starting 2,4-dinitrotoluene is equal to 100%.

EXAMPLE 4

10 g of γ—Al$_2$O$_3$ in the form of particles with a size of from 60 to 100 mesh are calcined in a current of air for 5 hours at a temperature of 500° C. and then impregnated with an aqueous solution of ammonium molybdate (10 ml containing 1 g of ammonium molybdate), dried at a temperature of 250° C. and heated in a current of air from 5 hours at a temperature of 500° C. Thereafter, these particles are impregnated with an aqueous solution of palladium chloride (1 g of palladium chloride per 10 ml of the solution), dried at a temperature of 250° C. and calcined for 5 hours at a temperature of 500° C. Particles of alumina with the deposited thereonto oxides of palladium and molybdenum are mixed with 0.05 g of magnesium oxide and compression molded into tablets which are then crushed to particles of about 1×1 mm.

A catalyst on a carrier, i.e. alumina, is obtained having the following chemical composition, namely: 40.3% by weight of palladium oxide, 57.0% by weight of molybdenum oxide, and 2.7% by weight of magnesium oxide.

Carbonylation of 2,4-dinitrotoluene is conducted under conditions similar to those described in the foregoing Example 1 using the catalyst as prepared in the present Example. The process temperature is equal to 210° C.

1.84 g of 2,4-toluylenediisocyanate are recovered by rectification (the yield is equal to 92%). The conversion of the starting 2,4-dinitrotoluene is 100%.

EXAMPLE 5

Carbonylation of 2,4-dinitrotoluene is conducted under conditions similar to those described in Example 1 in the presence of a catalyst having the following chemical composition: 77% by weight of palladium oxide, 19% by weight of molybdenum oxide and 4.0% by weight of magnesium oxide.

1.96 g of 2,4-toluenediisocyanate are recovered by rectification (the yield is equal to 98%). The conversion of the starting 2,4-dinitrotoluene is equal to 100%.

EXAMPLE 6

Carbonylation of 2,4-dinitrotoluene is conducted under conditions similar to those described in the foregoing Example 1 in the presence of a catalyst containing 65.7% by weight of palladium oxide, 33.0% by weight of molybdenum oxide, 1.3% by weight of magnesium oxide deposited onto alumina at a temperature of 210° C. 1.84 g of 2,4-toluylenediisocyanate are recovered by rectification (the yield is equal to 92%). The conversion of the starting nitrocompound is 100%.

EXAMPLE 7

Carbonylation of 2,4-dinitrotoluene is conducted under conditions similar to those described in Example 1 at a process temperature of 205° C. in the presence of a catalyst containing 40.3% by weight of palladium oxide, 57% by weight of molybdenum oxide, 2.7% by weight of magnesium oxide deposited onto a carrier of silica. 1.76 g of 2,4-toluenediisocyanate are recovered by rectification (the yield is equal to 83%). The conversion of the starting nitrocompound is equal to 100%.

EXAMPLE 8

Carbonylation of 2,4-dinitrotoluene is conducted under conditions similar to those described in Example 1 at a process temperature of 210° C. in the presence of a catalyst containing 40.3% by weight of palladium oxide, 57.0% by weight of molybdenum oxide and 2.7% by weight of magnesia deposited onto aluminosilicate. 1.70 g of 2,4-toluylenediisocyanate are recovered by rectification (the product yield is equal to 85%). The conversion of the starting 2,4-dinitrotoluene is equal to 100%.

EXAMPLE 9

Carbonylation of 1,3-dinitrobenzene is performed under conditions similar to those described in Example 1 in the presence of a catalyst containing 77% by weight of palladium oxide, 19% by weight of molybdenum oxide and 4% by weight of magnesium oxide. 1.46 g of 1,3-phenylenediisocyanate are recovered by rectification (melting point is 51° C.). The product yield is 98%. The conversion of the starting 1,3-dinitrobenzene is equal to 100%.

EXAMPLE 10

Carbonylation of 1,4-dinitrobenzene is conducted under conditions similar to those described in the foregoing Example 1 in the presence of a catalyst containing: 48.8% by weight of palladium oxide, 48.8% by weight of molybdenum oxide 2.4% by weight of magnesium oxide. 1.6 g of 1,4-phenylenediisocyanate are recovered by rectification (melting point of the product is 91° C.). The yield is 80%. The conversion of the starting 1,4-dinitrobenzene is 100%.

EXAMPLE 11

Carbonylation of 2,5-dinitroxylene is conducted under conditions similar to those described in Example 1 in the presence of a catalyst contining: 48.8% by weight of palladium oxide, 48.8% by weight of molybdenum oxide and 2.4% by weight of magnesium oxide. 1.8 g of 2,5-xyloylenediisocyanate are recovered by rectification (melting point of the product is 53° C.). The yield is 90%. The conversion of the starting nitrocompound is equal to 100%.

EXAMPLE 12

Carbonylation of 2,4-dinitromesitylene is conducted under conditions similar to those of Example 1 in the presence of a catalyst containing: 49.2% by weight of palladium oxide, 49.2% by weight of molybdenum oxide, 1.6% by weight of magnesium oxide. 1.8 g of 2,4-mesitylenediisocyanate are recovered by rectification; melting point of the product is 58° C. The yield is 90%. The conversion of the starting nitrocompound is equal to 100%.

EXAMPLE 13

Carbonylation of 1,4-dinitrodurene is conducted under conditions similar to those described in Example 1 in the presence of a catalyst containing: 49.2% by weight of palladium oxide, 49.5% by weight of molybdenum oxide, 1.6% by weight of magnesium oxide. 1.92 g of 1,4-durenediisocyanate (melting point is 112° C.) are recovered by rectification. The product yield is 96%. The conversion of the starting nitrocompound is equal to 100%.

EXAMPLE 14

Carbonylation of nitrobenzene is conducted under conditions similar to those of Example 1 in the presence of a catalyst containing: 48.8% of weight of palladium oxide, 48.8% by weight of molybdenum oxide and 2.4% by weight of magnesium oxide. 1.9 g of phenylisocyanate (boiling temperature is 162° C.) are recovered by rectification. The product yield is 95%; the conversion of nitrobenzene is equal to 100%.

EXAMPLE 15

Carbonylation of 1,3-dinitrobenzene is conducted under conditions similar to those of Example 1 in the presence of a catalyst containing: 48.8% by weight of palladium oxide, 48.8% by weight of molybdenum oxide and 2.4% by weight of magnesium oxide at a temperature of 170° C. The product, i.e. 1-nitrobenzene-3-isocyanate is recovered by rectification in the amount of 1.26 g (the yield is 63%). The conversion of the starting nitrocompound is 70% (selectivity is equal to 90%).

EXAMPLE 16

Carbonylation of 1,4-dinitrobenzene is conducted under conditions similar to those of Example 1 in the presence of a catalyst containing: 48.8% by weight of palladium oxide, 48.8% by weight of molybdenum oxide and 2.4% by weight of magnesium oxide. The process temperature is equal to 165° C. 1.32 g of 1-nitrobenzene-4-isocyanate is recovered by rectification. The product yield is 66% at the conversion of the starting nitrocompound equal to 72.%. Selectivity is equal to 91.6%.

EXAMPLE 17

Carbonylation of 4,6-dinitroxylene is conducted under conditions similar to those of Example 1 in the presence of a catalyst containing: 48.8% by weight of palladium oxide, 48.8% by weight of molybdenum oxide and 2.4% by weight of magnesium oxide. The process temperature is 170° C. 1.42 g of 1,3-dimethyl-4-nitrobenzene-6-isocyanate is recovered by rectification. The product yield is 71%; the conversion of the starting nitrocompound is equal to 75%. The selectivity is 94.6%.

EXAMPLE 18 (comparative)

Carbonylation of 2,4-dinitrotoluene is conducted under conditions similar to those mentioned in Example 1 in the presence of a catalyst, i.e. PdCl$_2$—Fe$_2$Mo$_7$O$_{24}$ (50:50). The yield of 2,4-toluenediisocyanate is only 40% at the 100% conversion of the starting nitrocompound.

EXAMPLE 19 (comparative)

Carbonylation of 2,4-dinitrotoluene is conducted under conditions similar to those of Example 1 in the presence of a catalyst, i.e. PdCl$_2$—Fe$_2$O$_3$—MoO$_3$ (2:1:2) deposited onto alumina, as in the prototype, but without modifying additives. The yield of 2,4-toluylenediisocyanate is only 25% at the 100% conversion of the starting nitrocompound.

What is claimed is:

1. A catalyst for carbonylation of aromatic nitrocompounds consisting of 1.6 to 4.0% by weight of an oxide of a metal selected from the group consisting of magnesium, calcium and zinc; 48.8 to 77.0% by weight of palladium oxide and 49.6 to 19% by weight of molybdenum oxide.

2. The catalyst of claim 1 supported on a carrier made of a material selected from the group consisting of alumina, silica, and aluminosilicate.

3. The catalyst of claim 2, wherein the carrier is present in an amount ranging from 76.7 to 85.1% by weight of the catalyst.

* * * * *